United States Patent [19]

Jarreau et al.

[11] Patent Number: 4,996,149

[45] Date of Patent: Feb. 26, 1991

[54] MICROBIOLOGICAL HYDROXYLATION PROCESS OF QUININE, QUINIDINE AND DERIVATIVES THEREOF

[75] Inventors: Francois X. Jarreau, Versailles; Robert G. Azerad, Ris Orangis; Thierry P. Ogerau, Voisins-le-Bretonneux, all of France

[73] Assignee: Nativelle S.A., Issy-les-Moulineaux Cedex, France

[21] Appl. No.: 37,351

[22] PCT Filed: Jul. 22, 1986

[86] PCT No.: PCT/FR86/00260

§ 371 Date: May 21, 1987

§ 102(e) Date: May 21, 1987

[87] PCT Pub. No.: WO87/00552

PCT Pub. Date: Jan. 29, 1987

[30] Foreign Application Priority Data

Jul. 23, 1985 [FR] France .............................. 85 11221

[51] Int. Cl.$^5$ ...................... C12P 17/16; C12P 17/12; C12N 1/14

[52] U.S. Cl. .................................. 435/119; 435/122; 435/931

[58] Field of Search ................ 435/119, 122, 822, 931

[56] References Cited

FOREIGN PATENT DOCUMENTS 0066489 12/1982 European Pat. Off. .

OTHER PUBLICATIONS

Eckenrode, F. M., "Microbiological Transformation of Quinidine", Journal of Natural Products, vol. 47, No. 5, (Sep.-Oct., 1984) pp. 882-884.

*Primary Examiner*—Richard A. Schwartz
*Assistant Examiner*—Mary E. Mosher
*Attorney, Agent, or Firm*—Milton B. Graff, IV; David L. Suter; Karen F. Clark

[57] ABSTRACT

A process for the regiospecific and stereospecific hydroxylation of quinine, quinidine and their derivatives, in position 3S, is characterized by the use of certain microorganisms being reacted on the compound to be hydroxylated.

5 Claims, No Drawings

MICROBIOLOGICAL HYDROXYLATION PROCESS OF QUININE, QUINIDINE AND DERIVATIVES THEREOF

This invention relates to a process for the hydroxylation of cinchona alkaloids, and more particularly to a new process for hydroxylation of quinine, quinidine, and their derivatives, by microbiological means.

Hepatic microsomal hydroxylation frequently constitutes one of the first stages of the metabolism of a foreign chemical compound introduced in a mammal's alimentary or blood circulation systems. Such hydroxylations, followed by other reactions, such as O-methylation or conjugation, are designed to render those substances more water-soluble, and therefore to accelerate their elimination. However, in certain cases, the hydroxylated compounds are more active, or more toxic, than the original molecule; this justifies interest in their identification, and therefore their preparation with a view towards the study of their activity.

Organic synthesis methods are obviously convenient for metabolites of simple substances, but the the chemical preparation of more complex (and optically active) molecules can require substantial effort and time.

Hydroxylations by microbiological means have already been developed considerably for many years in the field of steroids, where they have enabled obtaining, on an industrial scale, regio- and steroselectively hydroxylated products, resulting from specific oxidation of non functionalized carbon atoms. Such molecules would have required considerable synthesis efforts had it been necessary to utilize chemical methods. This method has since been applied to other families of molecules and it constitutes, in certain cases, a preferred way of obtaining new compounds, transposable to large scale production by utilization of classical fermentation techniques and equipment. Furthermore, it appears that microbic hydroxylations lead for each species to a frequently narrower range of metabolites than found in the mammals' systems, thus eliminating some separation problems; it is then sufficient to take advantage of the multiplicity of strains to reconstitute the various possibilities of hepatic metabolites.

However, in the field of alkaloids, rather few reactions of the said type have been described, and they relate in most cases to the non-nitrogenated part of the aromatic or non steroidic molecule. It is therefore both desirable and interesting to be able to carry out, in favourable conditions, the hydroxylation of nitrogenous alkaloid nuclei whose products have already been recognized as active metabolites. In particular, French patent No. 2,506,312 describes hydoxylated compounds of quinidine, such as hydroxy-3 dihydro-10,11 quinidine and its 3R and 3S epimers, which can be utilized therapeutically for the treatment of cardiac arrythmias. On the other hand, we are aware of the fact that quinine, whose pharmacological properties are known, and quinidine are two isomers, which differ in their configurations at the level of the carbons in positions 8 and 9.

The preparation of such active, optically pure, compounds, by a microbiological method, transposable to industrial scaling-up, therefore represents an objective of obvious interest as regards chemical hydroxylations, which lead to low yields and diastereoisomeric mixtures.

The object of this invention is therefore to provide a new process for microbiological hydroxylation of quinine, quinidine, and their derivatives, in particular their hydrogenated derivatives, in a regio- and stereospecific manner, so as to obtain optically pure compounds.

Another object of this invention is to provide a process of microbiolgical hydroxylation of quinine, quinidine, and their derivatives, susceptible of industrial application, and to supply optically pure compounds, with a satisfactory yield, by means of apparatus of conventional type.

The regiospecific and stereospecific microbiolgical hydroxylation process according to this invention allows hydroxylation, in the 3S position, of quinine, quinidine, and their derivatives, represented by formula (I):

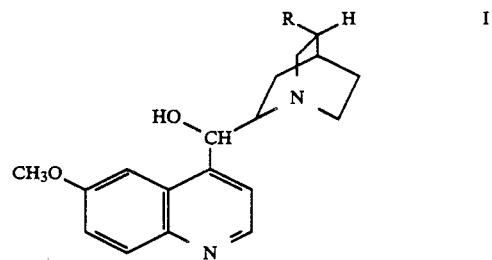

in which R represents an ethyl or vinyl group, to form the corresponding 3S-hydroxylated derivatives, of formula (II):

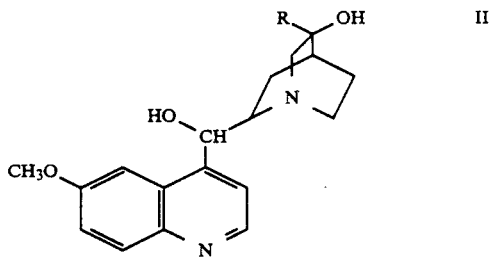

in which R has the same significance as above, by having a lower fungus type microorganism chosen from the group made up by *Aspergillus flavus, Aspergillus ochraceus, Aspergillus niger, Cunninghamella echinulata, Curvularia lunata, Mucor circinelloides, Mucor plumbeus, Penicillium purpurogenum, Rhizopus arrhizus* or the *Streptomyces rimosus* bacterial type act on compounds of type I.

In formula (I), above, R represents a vinyl radical in the case of quinine and quinidine, differing by the configuration of carbons in positions 8 and 9, and R represents an ethyl radical in the case of hydrogenated derivatives, that is to say, dihydroquinine and dihydroquinidine. The same remark applies to the hydroxylated derivatives of formula (II).

The hereinafter identified strains are preferably used: *Aspergillus ochraceus* (ATCC 1008), *Aspergillus flavus* (MMP 3249), *Aspergillus niger* (NRRL 599), *Cunninghamella echinulata* (NRRL 3655, MMP 2203), *Curvularia lunata* (NRRL 2380), *Mucor circinelloides* (CBS 108-16), *Mucor plumbeus* (MMP 430, CBS 111-07), *Rhizopus arrhizus* (ATCC 11145), *Streptomyces rimosus* (NRRL 2234), and *Penicillium purpurogenum* (MMP 222 bis), and the process consists in having one of the above microorganisms react on the compound to be hydroxylated.

The above references have their usual meanings, i.e., NRRL=Agricultural Research Culture Collection, Northern Regional Research Center, Peoria, Ill.; ATCC=American Type Culture Collection, Rockville, Md., USA; CBS=Centraal Bureau voor Shimmelcultures, Baarn Netherlands; MMP: Mycothèque du Muséum d'Histoire Naturelle, Paris, France.

According to the invention's hydroxylation process, it is preferable to have the microorganism grow in a culture medium containing assimilable sources of carbon, nitrogen and mineral salts, in aerobic fermentation conditions, and in immersed culture. The compound to be hydroxylated is added—preferably, under sterile conditions—to the medium, allowing incubation until obtaining a sufficient quantity of the hydroxylated product, and extraction is carried out with the usual techniques. Incubation can be carried out in an ordinary type fermentation tank, at a temperature range of between approximately 20° and 30° C., the medium having a pH close to 7. If need be, one can utilize a medium having a pH of approximately between 6 and 8, without appreciably changing the results.

The process utilized consists in growing the microorganisms in a suitable culture medium so as to obtain a well developed biomass; in addition to a source of assimilable carbon (dextrose, saccharose, starch, mannitol), in a 1 to 10% concentration, the said medium can contain a source of nitrogen, whether organic (peptones, asparagine, protein hydrolyzate), or mineral (ammonium salts, nitrates), and the necessary mineral salts, as well as vitaminic substances (such as those present in the "corn steep", yeast extract, . . . ); temperature can vary from approximately 20° to 30° C. according to the strains, and the culture is carried out with agitation. When growth is considered satisfactory, and generally when the hydrocarbon substrate is exhausted, that is to say, after about 2 to 5 days, the compound to be hydroxylated—as a solid, or dissolved in a small volume of a water miscible organic solvent (for example, ethanol-)—is added under sterile conditions, at a final concentration which can vary from 0.2 to several grams/liter according to the molecule or the strain. Incubation, which can be accompanied by a weak residual growth, is continued, with vigorous agitation to aerate the mixture, at the same temperatures, for a 2 to 40 days' period.

According to a variant of the process invention, the incubation of the compound to be hydroxylated is carried out with cells previously washed and resuspended in a buffered aqueous medium containing no carbon or nitrogen. Hydroxylation is then carried out after having grown the microorganism and after having collected the mycelium, in the absence of growth.

The extraction of the incubation products as well as that of the residual substrate is carried out by means of a water immiscible organic solvent (methylene chloride, chloroform, ethyl acetate, etc.), after elimination of the mycelium by filtration and saturating the solvent with salts (NaCl, $Na_2SO_4$).

The detection and identification of hydroxylation products can be carried out by thin layer chromatography on silica gel or by reverse-phase high-pressure liquid chromatography. The separation of the hydroxylated product from the remaining original substrate—if any—and its purification are carried out by the classical techniques of crystallization or chromatography on mineral adsorbents.

The purified hydroxylation products have been identified by comparison with the authentic (3S)-hydroxy products (prepared by chemical processes or described in the literature) in various chromatographic systems, as well as by the ordinary spectroscopic (UV, $^1H$- or $^{13}C$-NMR) and polarimetric techniques.

The results obtained are reported in the following examples, in which several strains of microorganisms capable of regio- and stereoselectively implementing these hydroxylations, starting from several of the substrates considered, with a variable rate of conversion, have been characterized. In addition to the essential advantage of hydroxylation selectivity, another advantage is the absence of formation of other metabolites in significant quantities, thus simplifying the purification and permitting the recycling of the substrate which may have not been metabolized.

The following examples illustrate the invention, without limiting its scope.

EXAMPLE 1

Hydroxylation of quinidine by *M. plumbeus*

A few drops of a suspension of *M. plumbeus* MMP 430 spores are added to 100 ml of medium A, described below, adjusted to pH7, in a 250 ml Erlenmeyer flask. Incubation is continued for 72 hours at 27° C. in a rotating agitator (327 RPM). A solution of 50 mg of quinidine in 1 ml of ethanol is then added under sterile conditions to the culture, and agitation is continued for 14 days under the same conditions. The culture is filtered on celite, the filtrate saturated with NaCl, brought to pH 10–12 by 2N NaOH, the extracted 6 times by methylene chloride. The dried and subsequently evaporated organic fractions are chromatographed on a preparative layer of silica gel, using as solvent $CHCl_2$-MeOH-$NH_4OH$ (85:14:1). The (3S)-3-hydroxy-quinidine band, identified by its fluorescence at 254 nm and its migration, which is smaller than that of quinidine, is scraped off and eluted by methanol. One obtains 1 mg of (3S)-3-hydroxy quinidine, identical with an authentic sample. Non-reacted quinidine is recovered in the same manner, and almost quantitatively (42 mg).

| Medium A: | |
|---|---|
| Corn steep | 10 grams |
| $MgSO_4,7H_2O$ | 0.5 grams |
| KCl | 0.5 grams |
| $NaNO_3$ | 2 grams |
| $FeSO_4,7H_2O$ | 0.02 grams |
| D-dextrose | 30 grams |
| $KH_2PO_4$ | 1 gram |
| $K_2HPO_4$ | 2 grams |
| Distilled water, a sufficient quantity to make | 1 liter. |

EXAMPLE 2

Hydroxylation of dihydroquinidine by *M. plumbeus*

The same incubation carried out on a similar culture of *M. plumbeus* CBS 111-07 with 1 g/liter of final concentration dihydroquinidine, yields after 20 days 5 mg of (3S)-3-hydroxy dihydroquinidine, identical to an authentic sample and 80 mg of recovered dihydroquinidine.

EXAMPLE 3

Hydroxylation of dihydroquinidine by *S. rimosus*

A few ml of a preculture of *S. rimosus* NRRL 2334 preculture are added to 100 ml of Medium B (described below), adjusted to pH7. Cultivation is carried out for 72 hours at 27° C.; 100 mg of dihydroquinidine dissolved in 1 ml of ethanol are added, and agitation is continued for 25 days under the same conditions. One obtains in the same manner 4 mg of (3S)-3-hydroxy dihydroquinidine and 85 mg of recovered dihydroquinidine.

| Medium B: | |
|---|---|
| Bacto Casamino acids Difco | 5 grams |
| Yeast extract | 3 grams |
| D-dextrose | 30 grams |
| Distilled water, a sufficient quantity to make | 1 liter. |

EXAMPLE 4

Hydroxylation of quinine by *C. echinulata*

The same incubation, carried out on a similar culture (medium A) of *C. echinulata* NRRL 3655, with quinine in a final 1 gram/liter concentration, yields, after 30 days, 9.5 mg of (3S)-3-hydroxy quinine identical to an authentic sample and 75 mg of recovered quinine. Also, the formation of small quantities of two other products (fluorescing at 254 nm) is evidenced.

EXAMPLE 5

Hydroxylation of dihydroquinine by *M. circinelloides*

The same incubation, carried out on a similar culture (medium A) of *M. circinelloides* CBS 108-16, with dihydroquinine at a final concentration of 1 gram/liter, yields after 36 days 17 mg of (3S)-3-hydroxy dihydroxyquinine identical with an authentic sample and 70 mg of recovered dihydro quinine.

EXAMPLE 6

Hydroxylation of dihydroquinidine by *M. plumbeus*

Two 100 ml cultures of *M. plumbeus* MMP 430 in the same medium A as in example 1, are mixed, centrifuged, and the mycelium, washed under sterile conditions with a phosphate buffer containing 2 grams of $K_2HPO_4$ and 1 gram of $KH_2PO_4$ per liter of distilled water, is placed in 100 ml of the same buffer and incubated with dihydroquinidine at a final concentration of 0.5 gram/liter.

After 5 days of incubation at 27° C., 6.5 mg of (3S)-3-hydroxy dihydroquinidine and 40 mg of recovered dihydroquinidine are obtained by the usual techniques.

We claim:

1. A process for the regiospecific and stereospecific hydroxylation of a compound selected from the group consisting of quinine, quinidine dihydroquinine, and dihydroquinidine, in position 3S, comprising incubation of said compound with the microorganism *Mucor plumbeus*.

2. A process according to claim 1, wherein said microorganism is grown under conditions of aerobic fermentation in an immersed culture medium comprising sources of assimilable carbon, nitrogen, and mineral salts.

3. A process according to claim 2, wherein the pH of said culture medium is from about 6 to about 8.

4. A process according to claim 3, wherein said incubation is carried out directly with previously washed cells that are resuspended in a medium that does not contain any source of carbon or nitrogen.

5. A process according to claim 4, wherein said incubation is carried out in the temperature range of from 20° C. to 30° C.

* * * * *